United States Patent [19]

O'Toole

[11] Patent Number: 4,896,672

[45] Date of Patent: Jan. 30, 1990

[54] HARDWARE CORECTION SCHEME FOR INTER-FRAME IMAGE JITTER IN A SCANNING PROBE ULTRASOUND IMAGING SYSTEM

[75] Inventor: Robert K. O'Toole, Sandown, N.H.

[73] Assignee: Hewlett-Packard Company, Palo Alto, Calif.

[21] Appl. No.: 173,759

[22] Filed: Mar. 28, 1988

[51] Int. Cl.[4] ............................................. A61B 10/00
[52] U.S. Cl. .................................. 128/660.09; 73/620
[58] Field of Search .............................. 318/560, 621; 128/660.09, 660.10; 73/620, 629,633

[56] References Cited

U.S. PATENT DOCUMENTS

| | | | |
|---|---|---|---|
| 4,092,867 | 6/1978 | Matzuk | 128/660.1 X |
| 4,269,066 | 5/1981 | Fischer | 128/660.1 X |
| 4,316,390 | 2/1982 | Kretz | 73/620 |
| 4,622,501 | 11/1986 | Eventoff et al. | 128/660.09 X |
| 4,671,292 | 6/1987 | Matzuk | 128/660.09 |

Primary Examiner—Francis Jaworski
Attorney, Agent, or Firm—Frank R. Perillo

[57] ABSTRACT

Circuitry for reducing side to side jitter in an ultrasound imaging system using a transducer which is mechanically scanned back and forth to cover the area to be imaged. The circuitry includes a filter circuit for providing a correction signal to be added to the transducer position signal. The filter circuit provides a phase lead proportional to the rate of change of the transducer movement. This signal is scaled by a factor which varies linearly as the depth being imaged changes. The correction signal compensates for delays through the transducer positioning and driver circuitry and for depth dependant delays resulting from the movement of the transducer during the scanning operation.

4 Claims, 2 Drawing Sheets

HARDWARE CORECTION SCHEME FOR INTER-FRAME IMAGE JITTER IN A SCANNING PROBE ULTRASOUND IMAGING SYSTEM

FIELD OF THE INVENTION

This invention relates to ultrasound imaging systems, and more particularly to cardiac imaging systems in which a transducer is mechanically scanned over an angle to provide data representative of a sector image profile.

BACKGROUND OF THE INVENTION

In many cardiac ultrasound imaging systems, the transducer is a single-element crystal or probe which is mechanically scanned or rotated back and forth to cover a sector over an angle of 30 to 90 degrees. Acoustic signals are transmitted during the scanning and echoes from these acoustic signals are received to provide data representative of the density of tissue over the sector. Such ultrasound probes are typically driven by a closed loop system in which a signal representative of the probe position is compared to a command signal representative of the desired probe position to drive a motor which moves the probe. Typically, a short pulse burst is transmitted for each acoustic line. As the probe is swept through the sector, many acoustic lines are processed building up a sector-shaped image of the patient. The timing of each pulse burst is a function of the angular position of the probe, and it is desirable to fire the probe at exactly the same angular position for each acoustic line as the probe repeatedly scans through the sector. A sector image may be updated twice for each cycle of probe movement, once in each direction as the probe scans forward and then returns to the beginning position.

One problem with such systems is frame jitter in the final image. This is caused by small differences in the detected echoes between scans in opposite directions as the probe moves back and forth across the sector. Jitter manifests itself as an oscillating sideways movement of the image at a frequency equal to the probe scanning frequency. Reducing the amount of jitter improves the resolution with which objects may be detected and distinguished by an operator.

Two different factors contribute to this jitter. The first factor results from inherent delays in the electronics used to detect the position of the probe and to trigger the acoustical pulse used for imaging. Although these delays are relatively constant, the image displacement alternates between positive and negative directions as the probe reverses direction during each cycle.

A second factor contributing to jitter is a depth-dependant component. This effect results from the probe being constantly in motion between the time it transmits and receives returning echoes. Following the transmission of a pulse, the probe continutes to scan and is slightly displaced in position when the returning echoes are received This causes a displacement of the center of the scan line in the direction of the probe movement, resulting in a jitter in the final image as the probe rotation changes direction during each scan. The amount of this jitter is a function of both the probe velocity, probe beam pattern, and the depth from which the transmitter pulses are reflected back.

SUMMARY OF THE INVENTION

A solution to the above described jitter problem has been developed which effectively eliminates the majority of frame jitter while requiring relatively uncomplicated circuitry. The circuitry corrects for accumulated delays in the hardware by generating a correction signal proportional to the probe velocity. This signal is then summed with the signal representing the detected probe position to provide a composite signal which, when used to trigger individual pulses, corrects for jitter resulting from delays in the trigger circuitry. The circuitry will provide correction of jitter resulting from such delays regardless of the amplitude, frequency, or wave shape used to drive the probe movement. This technique is able to completely eliminate frame jitter caused by hardware delays in the triggering circuitry. Additionally, jitter resulting from the depth dependant component may be substantially reduced by properly scaling the correction signal as a function of the imaging depth.

The invention greatly improves the image quality of ultrasound imaging systems in which the probe is mechanically scanned. Since mechanically scanned probes are more often used transducer systems, the simplicity of the circuitry necessary to in relatively low cost systems, in contrast with phased-array implement the present invention is especially advantageous.

DESCRIPTION OF THE DRAWINGS

The following description of the invention by way of example will more fully illustrate the advantages and operation of the present invention when read in conjunction with the accompanying drawings of which.

DESCRIPTION OF THE PREFERRED EMBODIMENT

Figure 1:
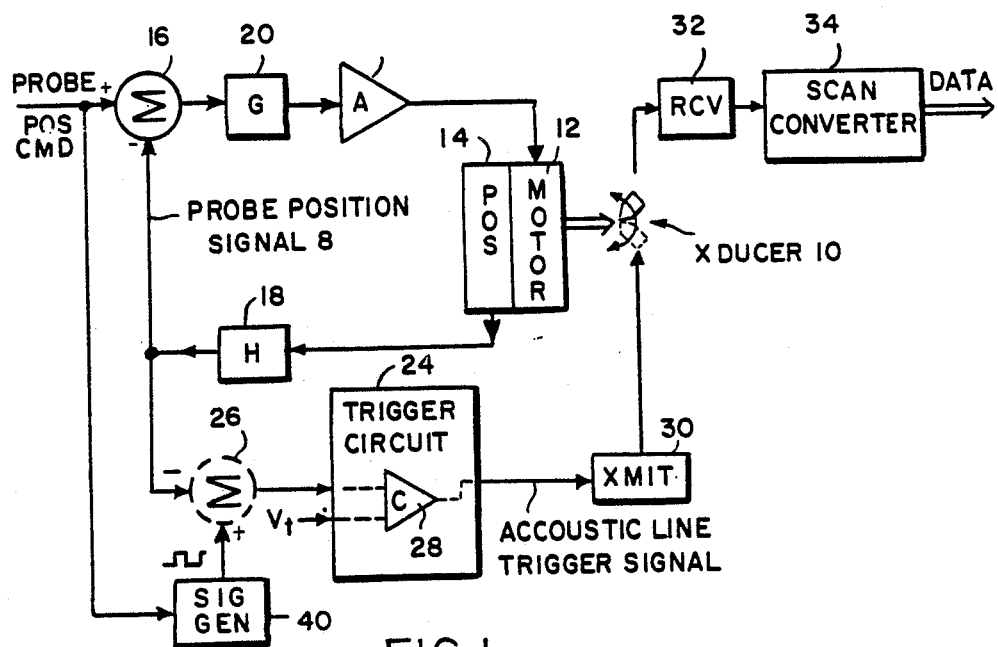
FIG. 1 illustrates a exemplary ultrasound imaging system with which the present invention may be used.

Referring to FIG. 1, there is shown a block diagram of a typical system for controlling the positioning and excitation of the transducer in an ultrasound imaging system in which the transducer is mechanically scanned back and forth over a sector. The transducer 10 pivots about an axis so that ultrasonic pulses transmitted thereby may be sent out over a sector which may typically cover up to 90 degrees. The position of transducer 10 is determined by a servo motor 12 which moves the transducer back and forth about the axis of rotation. A position indicating device 14 is also connected to transducer 10 and provides an position of the transducer. In the described embodiment, position sensor 14 includes a variable inductor coupled to the transducer. The assembly of the transducer, motor, and position indicator make up the probe.

A probe position command signal is applied to one input of a difference circuit 16. Depending on the particular application, different waveforms may be used for the probe position command to provide different scanning waveforms for transducer 10. These waveforms may include sinusoidial, sawtooth, and other waveforms.

The output from position sensor 14 is applied to signal processing circuitry 18 which suitably processes and scales the position sensor output to provide a voltage which is a linear representation of the transducer position. The output from circuit 18 represents the actual probe or transducer position as detected by sensor 14 and is applied to the negative input to difference circuit 16. The output from difference circuit 16 represents the difference or error between the probe position command and the actual probe position This error signal is applied through filter circuitry 20 and an amplifier 22 to motor 12 to position transducer 10. Filter circuitry 20 is a frequency compensation filter to ensure stability of the feedback loop which positions the transducer. The particular parameters of this filter depend on the individual application. Such filter circuits are well known in the art and are easily implemented by those of ordinary skill.

The probe position signal from circuit 18 is also applied to a trigger circuit 24 through an optional summer circuit 26, discussed in more detail below. Trigger circuit 24 compares the probe position signal representative of the instantaneous probe position with a voltage $V_t$ representative of the angle at which the next pulse is desired from transducer 10. The output from trigger circuit 24 is applied to a transmitter driver circuit 30 which, in response to a trigger signal, causes transducer 10 to emit a pulse at the desired frequency. The $V_t$ signal is continually updated during a scan and thus sequentially represents the individual positions during each scan at which a pulse is desired from transducer 10. In the described embodiment, transducer 10 is driven at a frequency which ranges from 2.5 MHz to 10 MHz, and the pulse width of each transmitted pulse is approximately two cycles of the transmit frequency. The angle over which transducer 10 is scanned typically ranges from 30 to 90 degrees and a typical scan will include approximately 120 pulses from transducer 10, each pulse producing a line in the final image derived from the transducer. Transducer 10 is scanned at a rate which ranges from 10 to 22.5 Hz.

Acoustic pulses from the transducer are reflected by changes in the density of tissue or objects in its path. These reflections are received by the transducer which produces a voltage in response thereto. This voltage is applied to receiving circuitry 32 which demodulates the received pulses and applies signals representative of the detected objects to a scan converter circuit 34. Scan converter circuit 34 processes the received echo signals and provides data representative of the received echoes which is used to provide an image of the scanned area.

One problem inherent with the circuitry of FIG. 1 is the result of delays in the electronic circuitry used to implement filter 18 and trigger circuit 24. Trigger circuit 24 essentially performs a comparison function between the probe position signal and the $V_t$ signal Ideally, trigger circuit 24 would produce an output pulse instantaneously when the probe position equals the probe position represented by the $V_t$ signal for the next scan line. In actual practice, there is an unavoidable delay in the signal path from signal detector 14 through filter 18 and trigger circuit 24. Due to these delays, there is an error between the actual position of transducer 10 and the indicated probe position as represented by probe position signal 8. This error produces a jitter effect in the image produced from echoes received by the transducer.

Figure 2A:
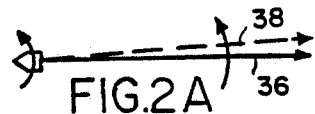
FIGS. 2A and 2B are useful in explaining errors caused by delays in the trigger circuit electronics.
Figure 2B:
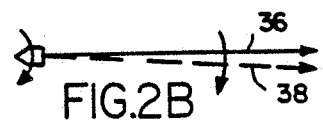

Referring to FIGS. 2A and 2B, lines 36 represent the desired path for a pulse from tranducer 10 and dotted lines 38 represent the actual path that the pulse follows. The actual path is slightly offset from the desired path due to the above described delays. In FIG. 2A, the transducer is rotating in a counter-clockwise direction, and the actual path is displaced upwardly from the desired path. In FIG. 2B, the transducer is rotating in a counter clockwise direction, and the actual path is displaced downwardly from the desired path. Thus, as transducer 10 scans back and forth, the delay through circuits 24 and 30 will cause the actual path for echoes corresponding to each scan line to alternately be offset in opposite directions. This causes a side-to-side jitter in the final image. The angular offset and resulting jitter is proportional to the angular velocity of transducer 10 and to the delay throughout the circuitry.

Prior art circuitry has provided for crude compensation of this delay by means of a summer circuit 26 which sums a square wave signal from a signal generator 40 with the probe position signal. Since the amount of delay is proportional to the transducer velocity, the delay will be a constant value so long as the angular rotation of the transducer is linear with respect to time. Signal generator 40 provides a square wave output whose frequency is equal to and synchronized with the scanning frequency of the transducer. By appropriately scaling the square wavefrom signal generator 40, trigger circuit 24 is activated earlier than it otherwise would be by an amount equal to the delay.

Figure 4:
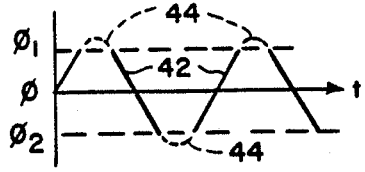
FIG. 4 represents the variation in probe angle with time.

The compensation scheme shown in FIG. 1 requires that the transducer angular velocity be constant. This has several disadvantages. First, the possible waveforms for the probe position command are limited to those which have linear segments over the scanned sector. Since transducer 10 has a finite mass, its angular momentum cannot be instantaneously reversed. Referring to FIG. 4, the angular position $\phi$ of the transducer 10 is shown for a typical system using the square wave correction scheme described above. Some finite time is required for the transducer to reverse position, as shown by dotted segments 44, and during these times, the square wave signal from signal generator 44 will not properly compensate for the delay through the trigger circuitry. Thus, either the edges of the image will be degraded, or the effective image will be limited to a scanning angle less than the total scanning angle of the transducer. More importantly, the circuit does not provide proper compensation for non-linear probe position command signals or for any deviations in the probe's trajectory from the commanded linear trajectory.

An additional phenomenon which causes jitter in the image is a depth-dependant component which results from the fact that the probe and transducer are constantly in motion between the time a pulse is transmitted and received, as described in the following explanation.

Figure 3A:
FIGS. 3A, 3B and 3C illustrate the depth-dependant effect.
Figure 8:
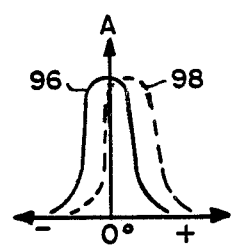
FIG. 8 is a representative curve of transducer sensitivity versus angle from the center line.

An ultrasonic transducer typically has a high sensitivity over a small angle on either side of the transducer's centerline. In FIG. 8, the solid curve 96 represents the transducer sensitivity as a function of this angle Referring to FIG. 3A, transducer 10 is shown transmitting acoustic waves 100 which cover a small angle. Although in actual practice, the transducer sensitivity falls off continuously at each edge, for purposes of this explanation the transducer will be assumed to have a fixed sensitivity over the arc 100 and to be non-responsive at angles outside this arc.

Figure 3B:
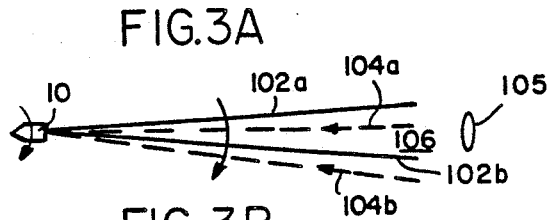

FIG. 3B represents the situation which occurs when the transducer is scanning in a clockwise direction. The transducer 10 transmits a short pulse at the excitation frequency which propagates along the path between solid lines 102a and 102b in FIG. 3B The signals are reflected by changes in tissue density, as represented by object 105, and return to the transducer. By the time the echoes reach transducer 10, however, the transducer has rotated so that its angle of reception has changed to that represented by the area between dotted lines 104a and 104b. The total sensitivity of the transducer is the product of its transmit and receive sensitivity. Thus, for the approximation shown in FIG. 3B in which the transducer is assumed to have zero sensitivity outside of the two angles shown, the transducer will only detect objects in area 106 between dotted line 104a and solid line 102b. Thus the area of sensitivity is displaced in a clockwise direction from the transducer's centerline at the time it transmits acoustic signals. In actual practice, the result is that the *total* sensitivity of the transducer, which is the product of the transmit and receive sensitivities, is displaced from the centerline of the transducer in the direction of the transducer movement, as represented by dotted curve 98 in FIG. 8.

Figure 3C:
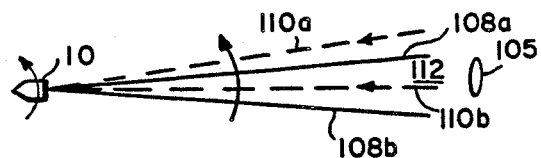

FIG. 3C represents the same situation when transducer 10 is moving in a counter-clockwise direction. Solid lines 108a and 108b represent the transducer's area of maximum sensitivity when it transmits. Dotted lines 110a and 110b represent the area of the tranducer's maximum sensitivity when it receives a pulse reflected by an object such as 105. The area 112 between lines 108a and 110b represent the area of maximum sensitiviy for the combined transmit and receive function. It can be seen from FIG. 3C that area 112 is displaced in a counter-clockwise direction from the center of the area of maximum sensitivity during the transmitting phase. -p Thus, the area of maximum transducer sensitivity for a rotating transducer will be displaced slightly towards the direction of rotation. This results in a side-to-side jitter in the final image with each change in scanning direction. The magnitude of this jitter is a function of the depth from which signals are reflected, since the angle through which the transducer moves between transmitting and receiving pulses from an object 105 is proportional to the distance that that object is from the transducer and thus is proportional to the imaging depth.

Figure 5:
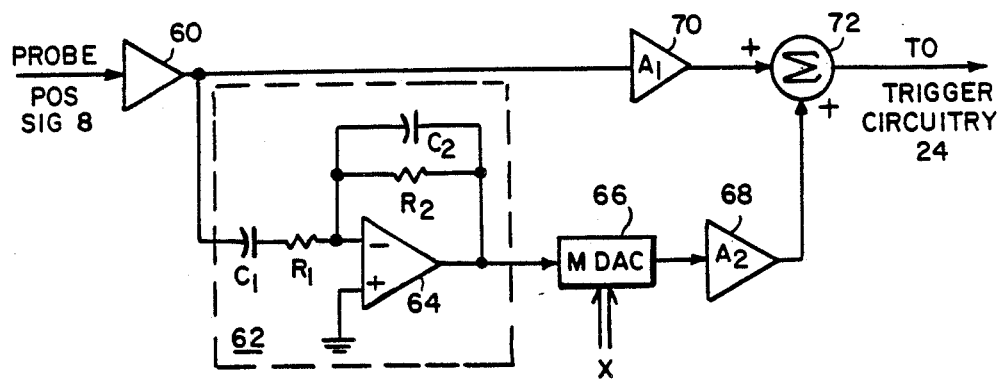
FIG. 5 is a circuit diagram showing one implementation of the present invention.

Referring to FIG. 5, there is shown a circuit which compensates for the delays caused by the electronic circuit response time and the depth dependant delay. In FIG. 5, the probe position signal 8 is applied via a buffer amplifier 60 to a filter circuit 62. Filter circuit 62 includes series-connected capacitor $C_1$ and resistor $R_1$ in series between the input to the filter circuit and the inverting input to an operational amplifier 64. The non-inverting input to op-amp 64 is grounded. The output signal from op-amp 64 is fed back to the inverting input via parallel-connected resistor $R_2$ and capacitor $C_2$.

The output from filter 62 is applied to the reference input of a multiplying digital-to-analog converter (MDAC) 66. A digital value represented "X" in FIG. 5 is applied to the digital inputs of MDAC 66. Thus, MDAC 66 provides a digitally-controlled, variable gain amplifier. The output from MDAC 66 is applied via a scaling amplifier 68 to one input of a summer circuit 72. In the described embodiment, MDAC 66 is an 8-bit converter, and the digital values applied to its input range from approximately 80 to 200 resulting in a gain of approximately 0.3 to 0.8. The manner in which the particular value of X is determined is described below.

The probe position signal from buffer amplifier 60 is directly applied to a second input to summer circuit 72 via a second scaling amplifier 70. The output from summer circuit 72 is applied to trigger circuit 24 to initiate a scan line. This signal consists of the probe position signal 8 scaled by the gain $A_1$ of amplifier 70 to which is added a compensation value determined by filter 62, and the gain of MDAC 66 and scaling amplifier 68. This value compensates for the effects of the electronic delay and depth-dependant delay factors, as described in more detail below.

The transfer function of the filter 62 is given by the following equation:

$$\frac{V_{OUT}}{V_{IN}} \alpha \frac{sR_2C_1}{(sR_2C_2 + 1)(sR_1C_1 + 1)}$$

It can be seen from the equation that the filter provides a phase lead at low frequencies resulting from the zero at zero frequency and includes two poles at the frequencies determined by time constants $R_1 C_1$ and $R_2 C_2$.

Figure 6:
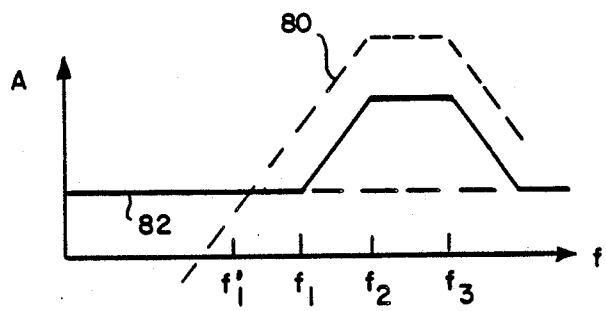
FIG. 6 is a frequency response curve for the circuit of FIG. 6.

Referring to FIG. 6, the frequency response of filter circuit 62 is represented by the dotted curved labelled 80. The frequency response increases up to the frequency of $f_2$ where the first pole causes it to level off until the frequency $f_3$ where the second pole results in a roll off at higher frequencies. In the described embodiment, $f_2$ is determined by $R_1$ and $C_1$ and is equal to 2 kHz. The $f_3$ pole is determined by $R_2$ and $C_2$ and is equal to 5.6 kHz.

Figure 7:
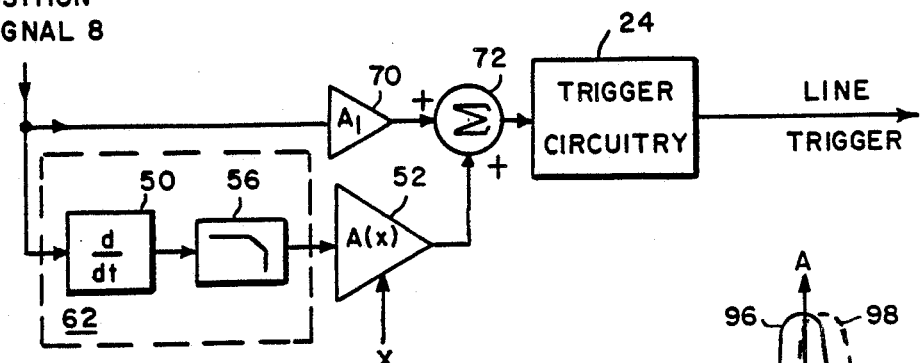
FIG. 7 is a block diagram of the embodiment of FIG. 5 invention.

The operation of the circuit of FIG. 5 may be more easily understood by reference to the block diagram shown in FIG. 7. In FIG. 7, the probe position signal 8 is applied to filter 62. The series connected network $C_1$ $R_1$ effectively operates as a differentiator circuit and is represented by block 50 in FIG. 7. The two-pole roll off of filter 62 is represented by low pass filter 56. The output from filter 62 is applied to a variable gain amplifier 52 representing the gain through MDAC 66 and scaling amplifier 68. The output from this circuitry is summed with a scaled probe position signal 8 from scaling amplifier 70 by summer 54.

The operation of differentiator circuit 50 provides a phase lead which is proportional to the derivative, and hence the scanning frequency, of the probe. Thus, as the probe speed increases, the delay compensation increase proportionally. This is the desired response to compensate for the fixed delay resulting from delays of the electronic circuitry. As the probe scanning frequency increases, the fixed delay results in a greater angular lag between the desired trigger time and the uncompensated trigger signal. Two pole filter circuit 56 filters out high frequency noise and also limits the high frequency response of differentiator circuit 50.

Referring to FIG. 6, solid line 82 shows the frequency response of the entire circuit of FIGS. 5 and 7 for a fixed value of gain from MDAC 66. At low frequencies, the frequency response is constant due to the unfiltered probe position signal applied to summer 72 via scaling amplifier 70. At frequency $f_1$, the increasing amplitude of the signal from filter 62, due to differentiator 50, exceeds the value of the signal from amplifier 70, resulting in a rising frequency response. At the first pole $f_2$ of filter 56, the frequency response levels off. Frequencies above the second pole $f_3$ are rolled off to eliminate high frequency noise.

By changing the gain of MDAC 66 in FIG. 5, represented by amplifier 52 in FIG. 7, the frequency $f_1$ at which the filtered signal applied to summer 72 exceeds the scaled probe position signal from amplifier 70 may be changed. Thus, increasing the gain of MDAC 66 moves the upper portion of the curve 82 to that represented by dotted curve 80 in FIG. 6. This effectively changes the low frequency break point $f_1$ of the circuit and changes the lead compensation provided by filter circuit 62. The $f_2$ and $f_3$ frequencies remain unchanged, however. In the described embodiment, the value of $f_1$ may be varied between 1 kHz and 2 kHz by changing the gain of MDAC 66. The frequency of $f_2$ and $f_3$ are not critical. All three poles contribute the phase shift. However, the leading phase shift from $f_1$ dominates the phase lags from $f_2$ and $f_3$ at the probe scanning frequencies of 10–22.5 Hz.

The particular value of gain chosen for MDAC 66 depends upon the depth of the area being imaged and the response of the particular probe type being used. These values are determined by measuring the depth dependant delay for each probe type at two depths, for example four centimeters and twenty centimeters, and linearly interpolating for depths between these values.

There has been described a new and useful circuit and method for providing compensation for delay effects which cause jitter in ultrasonic imaging systems. It should be appreciated that modifications will be made to the exemplary embodiments described herein in applying the teachings of the present invention to different applications. Accordingly, the present invention should not be limited by the description herein of particular embodiments, but rather should be interpreted only in accordance with the following claims.

What is claimed is:

1. In an acoustic imaging system having a moving transducer for transmitting and receiving a series of acoustic signals along a plurality of acoustic paths covering an area to be scanned to provide imaging data representative of the density of the scanned area, transducer positioning and driving circuitry, comprising:

transducer driving means, responsive to a trigger signal applied thereto, for applying signals to the transducer to cause an acoustic signal to be transmitted thereby;

means for moving the transducer with a cyclical motion so that acoustic signals transmitted by the transducer cover a scanned area;

means, coupled to the transducer, for providing a position signal representative of the transducer position;

trigger means, responsive to first and second signals for applying a trigger signal to the transducer driving means when the first and second signals are equal, the second signal being representative of the transducer position at which the next acoustic signal is to be transmitted;

compensation means, responsive to the position signal, for generating said first signal, including:

means, responsive to the position signal, for providing a scaled position signal proportional to the position signal;

means, responsive to the position signal, for generating a correction signal representative of the rate of change of the position signal; and means for adding the scaled position signal and the correction signal to provide said first signal.

2. The apparatus of claim 1 wherein the correction signal generating means includes:

differentiator circuit means for taking the time derivative of the position signal to provide an output signal representative thereof;

a low pass filter, to which is applied the differentiator circuit means output signal; and means for scaling the low pass filter output signal to provide said correction signal.

3. The apparatus of claim 2 wherein the low-pass filter includes at least 2 poles, the frequencies of which are higher than the frequency of the transducer cyclical motion.

4. The apparatus of claim 1 wherein the correction signal generating means further includes means responsive to a signal representative of the distance from the transducer of the area being scanned, for multiplying the correction signal by a scale factor which varies as linear function of said distance.

* * * * *